United States Patent [19]

Zimmerman

[11] 4,191,771

[45] Mar. 4, 1980

[54] ANALGESIC METHOD USING 1,3,4-TRISUBSTITUTED-4-ARYLPIPERIDINES

[75] Inventor: Dennis M. Zimmerman, Mooresville, Ind.

[73] Assignee: Eli Lilly and Company, Indianapolis, Ind.

[21] Appl. No.: 19,528

[22] Filed: Mar. 12, 1979

Related U.S. Application Data

[60] Continuation-in-part of Ser. No. 905,494, May 12, 1978, which is a division of Ser. No. 852,252, Nov. 17, 1977, Pat. No. 4,115,400, which is a division of Ser. No. 690,767, May 27, 1976, Pat. No. 4,081,450, which is a continuation of Ser. No. 503,581, Sep. 6, 1974, abandoned.

[51] Int. Cl.$^2$ ............... A61K 31/44; A61K 31/445

[52] U.S. Cl. .................................. 424/267; 424/263

[58] Field of Search .............................. 424/267, 263

[56] References Cited

U.S. PATENT DOCUMENTS

| | | | |
|---|---|---|---|
| 1,915,334 | 6/1933 | Salzberg et al. | 260/243 B |
| 2,075,359 | 3/1937 | Salzberg et al. | 424/250 |
| 2,892,842 | 6/1959 | McElvain | 260/293.84 |
| 3,080,372 | 3/1963 | Janssen | 260/293.84 |
| 3,936,468 | 2/1976 | Yamamoto et al. | 260/293.84 |

*Primary Examiner*—Stanley J. Friedman
*Attorney, Agent, or Firm*—Charles W. Ashbrook; Arthur R. Whale

[57] ABSTRACT

1,3,4-Trisubstituted-4-arylpiperidines are used to impart analgesia and to treat narcotic addiction.

10 Claims, No Drawings

ANALGESIC METHOD USING 1,3,4-TRISUBSTITUTED-4-ARYLPIPERIDINES

CROSS REFERENCE TO RELATED APPLICATIONS

This is a continuation-in-part of Ser. No. 905,494, filed May 12, 1978, which is a division of Ser. No. 852,252, filed Nov. 17, 1977, now U.S. Pat. No. 4,115,400, which is a division of Ser. No. 690,767, filed May 27, 1976, now U.S. Pat. No. 4,081,450, which is a continuation of Ser. No. 503,581, filed Sept. 6, 1974, abandoned.

BACKGROUND OF THE INVENTION

Extensive research has been focused on agents that relieve pain and on their preparation. Interest has recently developed in compounds that display antagonistic activity against narcotic drugs, mainly for two reasons. First, it is desirable to have narcotic antagonist compounds which give rise to analgesia while at the same time having a greatly reduced abuse potential. Secondly, it is desirable to have compounds that are useful in the treatment of narcotic addiction. N-allyl-norcodeine is probably the first specific narcotic antagonist prepared and studied. It was synthesized by J. Pohl in 1914. Several similar compounds have been synthesized in an effort to prepare a long-acting orally effective antagonist. In general, all of these compounds are characterized by a relatively short duration of action, low oral effectiveness, and varying degrees of agonistic effects.

Several compounds of the piperidine class have been found to display interesting analogesic activity, and some have displayed varying degrees of antagonist activity, as described for example by Nurimoto and Hayashi, *Japan J. Pharmcol.* 23 743 (1973). Many 1,2,3-trialkyl-3-arylpiperidines have been prepared and evaluated as analogesic drugs; see for example U.S. Pat. Nos. 3,043,845 and 2,892,842. Very interesting antagonistic properties have been displayed by a group of 1,4-disubstituted-4-arylpiperidines, as described by Langbein, et al., *Narcotic Antagonists, Advances in Biochemical Psychopharmacology*, Vol. 8, Raven Press, New York, 1974, pp. 157–165. Several 1-methyl-4-alkyl-4-(3-hydroxyphenyl)piperidines were prepared and evaluated as analogesics by McElvain, U.S. Pat. No. 2,892,842.

Very little work has been directed to the preparation of 1,3,4trisubstituted-4-arylpiperidines, presumably because of the difficulty of their preparation. McElvain et al. reported the preparation of 1,3,4trimethyl-4-(2-methoxyphenyl)piperidine as a biproduct in the synthesis of a 1,4-dialkyl-4-arylpiperidine; *J. Am. Chem. Soc.* 80, 3915 (1958). It was reported, however, that an ortho- or paramethoxyl group on the phenyl substituent rendered such compounds almost totally inactive as analgesics. Similarly, Janssen prepared several 1-aroyl-3,4-dialkyl-4-arylpiperidine derivatives which are useful as central nervous system depressants, U.S. Pat. No. 3,080,372.

It is an object of this invention to provide a process for preparing 4-arylpiperidines substituted in the 1, 3, and 4-positions with alkyl or alkenyl groups. It is a further object to provide such piperidines which display useful analgesic activity and which, in some cases, are potent narcotic antagonists. An additional object of the invention is to provide novel intermediates useful for preparing new piperidines.

SUMMARY OF THE INVENTION

In fulfillment of the above and other objects, the present invention provides compounds of the formula

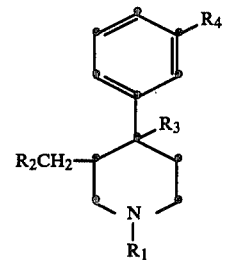

I

The invention further provides a process for preparing 1,3,4-trisubstituted-4-arylpiperidines comprising treating a 2,3-disubstituted-3-aryl-1-pyrroline with an alkylating agent to afford the corresponding 1,2,3-trisubstituted-3-arylpyrrolinium salt, reacting the salt so formed with diazonmethane to obtain the novel bicyclic pyrrolidinium salt having the general formula

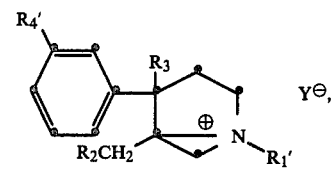

II heating the bicyclic pyrrolidinium salt to a temperature sufficient to effect a ring expansion to produce a 1,3,4-trisubstituted-4-aryl-1,4,5,6-tetrahydropyridinium salt, neutralizing the salt and reducing the tetrahydropyridine to the corresponding 1,3,4-trisubstituted-4-arylpiperidine. The piperidine so formed can be converted to other piperidines of the invention by standard procedures.

In the foregoing formulae, $R_1$ is hydrogen, $C_1$–$C_8$ alkyl, $C_4$–$C_8$ (cycloalkyl)alkyl, benzyl, $C_3$–$C_8$ alkenyl, $C_3$–$C_8$ alkynyl, or substituted alkyl;

$R_1'$ is a subgroup of $R_1$ which includes $C_1$–$C_8$ alkyl, $C_4$–$C_8$ (cycloalkyl)alkyl, and benzyl;

$R_2$ is hydrogen, $C_1$–$C_4$ alkyl, or $C_2$–$C_6$ alkenyl;

$R_3$ is $C_1$–$C_4$ alkyl, or $C_2$–$C_6$ alkenyl;

$R_4$ is hydrogen, hydroxy, $C_1$–$C_3$ alkoxy, or acyloxy;

$R_4'$ is a subgroup of $R_4$ consisting of hydrogen, hydroxy, and $C_1$–$C_3$ alkoxy; and $Y^\ominus$ is a non-nucleophilic anion.

Also included within the scope of this invention are the pharmaceutically acceptable acid addition salts and quaternary ammonium salts of the piperidines provided herein.

The invention also provides a method of treating narcotic addition which comprises administering an effective dose of a compound having the formula

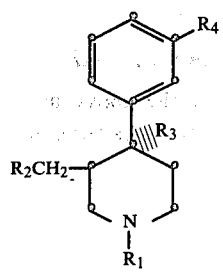

wherein: $R_1$ is $C_1$–$C_8$ alkyl, $C_4$–$C_8$ (cycloalkyl)alkyl, benzyl, $C_3$–$C_8$ alkenyl, $C_3$–$C_8$ alkynyl or

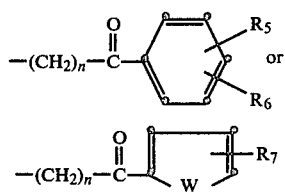

wherein:
n is 1, 2, or 3;
W is O or S;
$R_5$ is $C_1$–$C_3$ alkylthio, nitro, amino, trifluoromethyl, hydroxy, or $R_6$;
$R_6$ is hydrogen, $C_1$–$C_3$ alkyl, $C_1$–$C_3$ alkoxy, or halogen;
$R_7$ is hydrogen or methyl;
$R_2$ is hydrogen, $C_1$–$C_4$ alkyl, or $C_2$–$C_6$ alkenyl;
$R_3$ is $C_1$–$C_4$ alkyl or $C_2$–$C_6$ alkenyl; and
$R_4$ is hydrogen, hydroxy, $C_1$–$C_3$ alkoxy; $C_1$–$C_{12}$ alkanoyloxy or

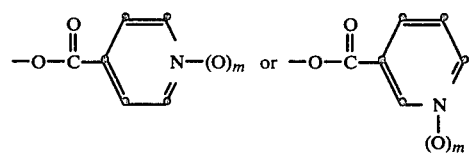

in which m is 0 or 1.

Additionally provided is a method for imparting analgesia comprising administering to a subject an effective dose of a cis-1,3,4-trisubstituted-4-arylpiperidine of the formula:

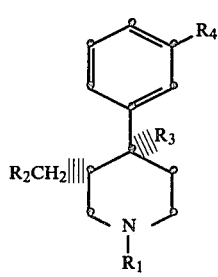

wherein: $R_1$ is $C_1$–$C_8$ alkyl, $C_3$–$C_8$ alkenyl, $C_3$–$C_8$ alkynyl, $C_4$–$C_8$ (cycloalkyl)alkyl,

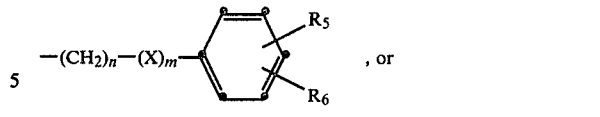

wherein:
n is 1, 2, or 3;
m is 0 or 1;
X is

$CH=CH$, S, O or $NR_8$,
wherein: $R_8$ is hydrogen, $C_1$–$C_4$ alkyl or $C_1$–$C_4$ alkanoyl;
Z is

or $CH=CH$;
W is O or S;
$R_5$ is $C_1$–$C_3$ alkylthio, nitro, amino, trifluoromethyl, hydroxy, or $R_6$;
$R_6$ is hydrogen, $C_1$–$C_3$ alkyl, $C_1$–$C_3$ alkoxy, or halogen;
$R_7$ is hydrogen or methyl;
$R_2$ is hydrogen, $C_1$–$C_4$ alkyl, or $C_2$–$C_6$ alkenyl;
$R_3$ is $C_1$–$C_4$ alkyl or $C_2$–$C_6$ alkenyl; and
$R_4$ is hydrogen, hydroxy, $C_1$–$C_3$ alkoxy, $C_1$–$C_{12}$ alkanoyloxy, or

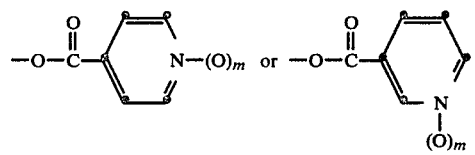

wherein m is 0 or 1; and the pharmaceutically acceptable salts thereof.

DETAILED DESCRIPTION OF THE INVENTION

The compounds provided by this invention include those having the general structural formula

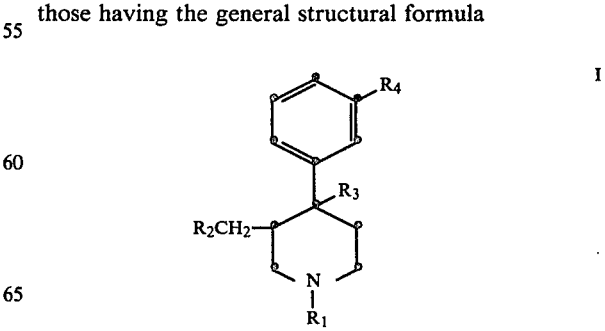

and the pharmaceutically acceptable salts thereof.

$R_1$ in the above formula is hydrogen, $C_3$-$C_8$ alkenyl, $C_3$-$C_8$ alkynyl, substituted alkyl, $C_1$-$C_8$ alkyl, $C_4$-$C_8$ (cycloalkyl)alkyl, or benzyl.

The term "$C_1$-$C_8$ alkyl" refers to straight or branched carbon chains having no more than eight carbons. Examples of $C_1$-$C_8$ alkyl groups include methyl, ethyl, isopropyl, isobutyl, pentyl, 3-methylheptyl, octyl, and the like. "$C_3$-$C_8$ alkenyl" refers to groups having the formula $CH_2A$, wherein A is $C_2$-$C_7$ alkenyl. Examples of $C_3$-$C_8$ alkenyl groups include allyl, 3-butenyl, 3-methyl-2-butenyl, 2,3-dimethyl-2-butenyl, 5-octenyl, and the like. Similarly, "$C_3$-$C_8$ alkynyl" refers to groups having the formula $CH_2B$, wherein B is $C_2$-$C_7$ alkynyl. Examples of such $C_3$-$C_8$ alkynyl groups include 2-propynyl, 3-butynyl, 4-hexynyl, 4-methyl-5-hexynyl, 6-octynyl, and the like. Typical examples of $C_4$-$C_8$ (cycloalkyl)alkyl groups include cyclopropylmethyl, 1-cyclopropylethyl, 2-cyclopropylethyl, cyclobutylmethyl, 2-cyclobutylpropyl, (2-methylcyclobutyl)methyl, 2-cyclohexylethyl, and the like. The term "substituted alkyl" refers to groups having the formula

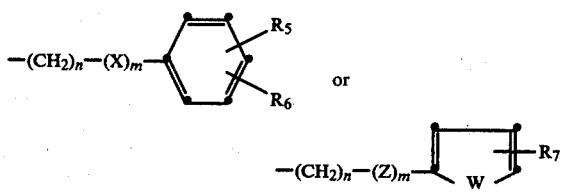

in which n is 1, 2, or 3; m is 0 or 1; X is

CH=CH, S, O, or $NR_8$; Z is

CH=CH; W is O or S; $R_5$ is $C_1$-$C_3$ alkylthio, nitro, amino, trifluoromethyl, hydroxy, or $R_6$; $R_6$ is hydrogen, $C_1$-$C_3$ alkyl, $C_1$-$C_3$ alkoxy, or halo; $R_7$ is hydrogen or methyl; and $R_8$ is hydrogen, $C_1$-$C_4$ alkyl, or $C_1$-$C_4$ alkanoyl. "Halo" as used herein is fluoro, chloro, bromo, or iodo. Examples of typical substituted alkyl groups of the above formulae include 3-phenylpropyl, benzoylmethyl, 3-hydroxy-3-phenylpropyl, 3-phenyl-2-propenyl, 2-phenylthioethyl, 2-phenoxyethyl, 3-N-phenylaminopropyl, 2-(3-methylthiophenyl)ethyl, 3-(4-nitrophenyl)propyl, (3-aminophenyl)methyl, (4-trifluoromethylphenyl)methyl, 2-(3-hydroxyphenyl)ethyl, (3,4-dimethylphenyl)methyl, (3,4-dimethoxyphenyl)methyl, (3,4-dichlorophenoxy)methyl, 2-(3-nitro-4-chlorophenyl)ethyl, [N-(3,4-dichlorophenyl)-N-acetyl]aminomethyl, (2-thiophene)methyl, 2-(3-thiopene)ethyl, 2-(2-thiophene)-2-oxo-ethyl, 2-(2-furyl)-2-hydroxyethyl, 3-[2-(5-methylthiophene)]-2-propenyl, and the like.

$R_2$ in the above formula is hydrogen, $C_1$-$C_4$ alkyl, or $C_2$-$C_6$ alkenyl. Examples of $C_1$-$C_4$ alkyl include methyl, ethyl, isobutyl, and n-butyl. Typical $C_2$-$C_6$ alkenyl groups include vinyl, allyl, 4-methyl-3-pentenyl, 5-hexenyl, and the like.

$R_4$ in formula I is hydrogen, hydroxy, $C_1$-$C_3$ alkoxy, or acyloxy. The term "$C_1$-$C_3$ alkoxy" includes methoxy, ethoxy, propoxy, and isopropoxy. The term "acyloxy" refers to $C_1$-$C_{12}$ alkanoyloxy groups such as acetoxy, butyroxy, pentanoyloxy, isohexanoyloxy, 4-butyloctanoyloxy, lauroyloxy, and the like. The term "acyloxy" also refers to groups of the formulae

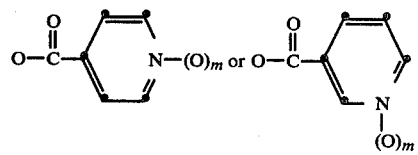

in which m is 0 or 1.

While most of the piperidines of this invention are conveniently prepared by the process described herinbelow, a preferred aspect of the invention comprises carrying out the process with pyrrolines bearing substituents which are not modified by any subsequent step of the reaction sequence and which can be easily manipulated to provide either compounds of the invention or intermediates therefor. In particular, the process is best carried out by alkylating a pyrroline with an alkyl, (cycloalkyl)alkyl, or benzyl moiety, which group is designated herein as $R_1'$ and represents a subgroup of $R_1$ of the above formula. Further, when carrying out the process, $R_4$ of the above formula is preferably limited to hydrogen, hydroxy, or alkoxy, which group of substituents is designated $R_4'$ and is a subgroup of $R_4$.

According to the process of this invention, piperidines of the formula

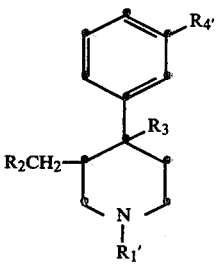

are prepared from a suitably substituted pyrroline starting material. The process can be carried out to provide a piperidine that is a useful pharmacological agent in itself, or alternatively the piperidines formed by the process can be converted to other useful piperidines of the invention. For example, the process can be carried out to provide a piperidine of the above formula wherein $R_1'$ is a readily removable group, such as methyl or benzyl for instance, and wherein $R_4'$ is a group which can easily be modified, such as a methoxyl group for example. A methyl or benzyl group can be removed by standard method,s and the methoxyl group can be converted to a hydroxyl group, thereby providing a 3,4-disubstituted-4-(3-hydroxyphenyl)piperidine which is an important intermediate that can be converted to other novel piperidines of the invention by standard procedures, such as alkylation of acylation for example.

It will be noted in the above formulae that the piperidines of the invention occur as stereochemical isomers by virtue of the substituents at the 3 and 4-positions. In particular, an alkyl group, for example, at the 3-position can be situated either in a cis position or trans position relative to an alkyl group, for example, at the 4-position.

In general, the cis piperidines, wherein $R_2CH_2$ and $R_3$ in the above formulae are situated cis to one another, exhibit narcotic agonist activity. The trans isomers exhibit distinct narcotic antagonist activity in addition to showning agonist effects.

The piperidines of this invention form pharmaceutically acceptable acid addition salts with a wide variety of inorganic and organic acids. The particular acid used in salt formation is not critical; however, the corresponding salt that is formed must be substantially non-toxic to animal organisms. Typical acids generally used include sulfuric, hydrochloric, hydrobromic, phosphoric, hydroiodic, sulfamic, citric, acetic, maleic, malic, succinic, tartaric, cinnamic, benzoic, ascorbic, and related acids. The piperidines additionally form quaternary ammonium salts with a variety of organic esters of sulfuric, hydrohalic, and aromatic sulfonic acids. Among such esters are methyl chloride, ethyl bromide, propyl iodide, butyl bromide, allyl iodide, isobutyl chloride, benzyl bromide, dimethyl sulfate, diethyl sulfate, methyl benzenesulfonate, ethyl toluenesulfonate, crotyl iodide, and the like.

According to the present invention a 2,3-disubstituted-3-arylpyrroline is alkylated in the 1-position to provide a 1,2,3-trisubstituted-3-arylpyrrolinium salt. Reaction of the pyrrolinium salt with diazomethane affords a bicyclic system, namely a 1,2,3-trisubstituted-3-aryl-1,2-methylenepyrrolidinium salt. the bicyclic salt is heated to a temperature of about 100° to about 250° C. to effect a ring expansion to the corresponding 1,3,4-trisubstituted-4-aryl-1,4,5,6-tetrahydropyridinium salt. Neutralization and reduction of the tetrahydropyridinium salt provides a 1,3,4-trisubstituted-4-arylpiperidine of the invention. The piperidines so formed are useful pharmacological agents in themselves, or if desired, they can be modified to form other novel and active piperidines of the invention, for example by removal of the 1-substituent and re-alkylation with a different substituent. The novel process disclosed herein can be readily understood by referring to the reaction sequence outlined in Scheme I.

practically any alkylating agent can be used to alkylate the pyrroline; however, the alkyl group that is added to the pyrroline should be one that is stable throughout the process of the invention. For example, the alkyl group should be stable to relatively high temperatures, to basic treatment, and to reduction, which reactions are discussed hereinbelow. Typically, the alkylating agent used in the present process is a compound of the formula $R_1'Y$, in which Y is a non-nucleophilic anion, and $R_1'$ has the above defined meaning.

A "non-nucleophilic anion," as used herein, refers to an anion which does not attack the bicyclic pyrrolidinium system that is formed in a subsequent step of the process by the reaction of diazomethane and the pyrrolinium salt. Examples of non-nucleophilic anions include tetrafluoroborate, fluorosulfonate, tetraphenylborate, perchlorate, and the like. Examples of alkylating agents which incorporate such non-nucleophilic anions include trimethyloxonium tetrafluoroborate, triethyloxonium tetraphenylborate, methyl fluorosulfonate, ethyl perchlorate, benzyl perchlorate, and the like. In practice, it is generally preferred to carry out the akylation with a more common and less expensive alkylating agent, for example, one which incorporates a more nucleophilic anion. Examples of nucleophilic anions include halide, alkyl and aryl sulfonates, and the like. When a nucleophilic anion is incorporated into the pyrrolinium salt, however, it must be replaced by a non-nucleophilic anion before reaction of the pyrrolinium salt with diazomethane. Typical alkylating agents commonly used include sulfates, halides, and aromatic sulfonates. Among such alkylating agents are methyl chloride, ethyl bromide, isobutyl iodide, pentyl iodide, octyl bromide, isooctyl chloride, cyclopropylmethyl iodide, cyclobutylmethyl bromide, dimethylsulfate, diisopropyl sulfate, benzyl bromide, benzyl iodide, ethyl toluenesulfonate, methyl toluenesulfonate, and related agents. The nucleophilic anion is then replaced by a non-nucleophilic anion as described hereinbelow. In a preferred aspect of the invention, the pyrroline is alkylated with a readily removable group, such as Scheme I

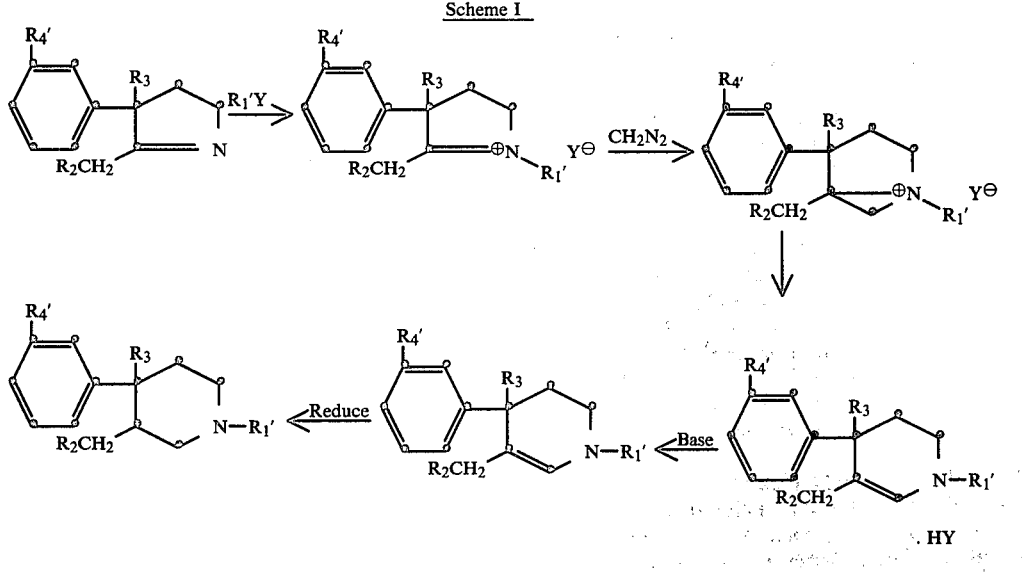

The first step of the present process comprises treating a 2,3-disubstituted-3-aryl-1-pyrroline with an alkylating agent to provide a 1,2,3-trisubstituted-3-aryl-1-pyrrolinium salt. It will generally be recognized that methyl or benzyl for example. The 1-methyl or 1-benzylpyrrolinium salt is converted to the corresponding piperidine through the steps of the present process. The 1-methyl or 1-benzyl piperidine that is formed is then converted to the 1-unsubstituted piperidine, which intermediate can be re-alkylated to provide the desired compound of the invention.

The alkylation of the pyrroline is preferably carried out in an unreactive organic solvent. Suitable solvents include ketones such as acetone, methyl ethyl ketone, diethyl ketone, or the like, as well as ethers such as diethyl ether, dipropyl ether, or dibutyl ether for example. More polar solvents such as, for example, dimethylformamide, dimethyl sulfoxide, hexamethylphosphoramide, or the like, are also suitable solvents for the alkylation reaction. The particular solvent selected for the reaction is not critical.

The alkylation reaction is generally carried out at a temperature below about 180° C., normally at a temperature between about 25° C. to about 160° C. The reaction is most conveniently carried out at the reflux temperature of the reaction solvent.

The amount of alkylating agent used is generally about an equimolar amount relative to the starting pyrroline; however, more alkylating agent can be used if desired. When less than an equimolar amount of alkylating agent is used, lower yields of the 1-alkyl-1-pyrrolinium salt are normally observed. Preferably, an excess of about 1 to about 15 percent molar excess of alkylating agent is used. The alkylation is substantially complete after about 1 to about 4 hours and any excess alkylating agent can be destroyed if desired by the addition of the appropriate amount of a hydrogen source, such as water or ethanol. For example, if an alkylating agent such as an alkyl sulfate or an alkyl oxoniumtetrafluoroborate is used, a proton source such as water can be added to the reaction mixture, and the destruction of any excess alkylating agent is normally complete within about 2 to about 18 hours when the reaction mixture is stirred at a temperature of about 25° to about 150° C. Alternatively, if the alkylating agent used was such that simple distillation would rid the reaction mixture of excess, for example if an agent such as methyl iodide were used, then removal of excess agent can be accomplished by evaporation.

The alkylated product, a 1,2,3-trisubstituted-3-aryl-1-pyrrolinium salt, can generally be isolated by removal of any water present in the reaction mixture and crystallization of the salt. When the salt so formed contains, as the anion, a non-nucleophilic anion, such as tetrafluoroborate or perchlorate for example, the salt can be isolated and used directly with diazomethane.

Alternatively, the pyrrolinium salt containing the nucleophilic anion, such as chloride or methanesulfate for instance, is preferably not isolated but is treated with a base while still in the alkylation reaction mixture, thereby providing a 2-alkylene pyrrolidine. More specifically, the alkylation reaction mixture is made alkaline by the addition of an aqueous alkali or alkaline earth metal hydroxide such as, for example, sodium hydroxide, potassium hydroxide, calcium hydroxide, or magnesium hydroxide. Other bases, such as ammonium hydroxide, or even organic bases, such as N-benzyltrimethylammonium hydroxide or triethylamine for example, can be used if desired. The alkylated pyrrolinium salt is converted, in the aqueous alkaline reaction mixture, into a 1,3-disubstituted-2-alkylene-3-arylpyrrolidine as a free base. The pyrrolidine is generally insoluble in the aqueous reaction mixture and can be extracted therefrom with any suitable organic solvent such as, for example, diethyl ether, ethyl acetate, chloroform, benzene, or the like. The solvent can be removed from the extracts and the pyrrolidine can be used without further purification, or alternatively can be further purified if desired by normal procedures such as distillation, chromatography, crystallization, or the like.

The 2-alkylene-1,3-disubstituted-3-arylpyrrolidine is next treated with a suitable acid, one wherein the anion is non-nucleophilic, to provide a 1,2,3-trisubstituted-3-aryl-1-pyrrolinium salt. Suitable acids include such acids as tetrafluoroboric acid, perchloric acid, tetraphenylboric acid, fluorosulfonic acid, and the like. The reaction between the pyrrolidine and a suitable acid is carried out in an unreactive organic solvent such as, for example, diethyl ether, dipropyl ether, tetrahydrofuran, ethyl alcohol, methyl alcohol, benzene, chloroform, dichloromethane, or the like. The solvent selected is not critical to the process. The reaction is generally carried out at a temperature below about 75° C., normally at a temperature of about 0° to about 50° C. Although the precise temperature of the reaction is not critical, the reaction is preferably carried out at about 15° C. to about 35° C. The amount of acid used is generally an equimolar amount relative to the starting pyrrolidine, although more, or less, can be used if desired. Preferably, the acid is added to the reaction mixture in quantities sufficient to maintain the pH of the reaction mixture at about pH 3 to about pH 5. The reaction can be followed by monitoring the pH of the solution, for example, by testing the acidity with an appropriate acid indicator such as congo red or bromophenol blue for example. The reaction is substantially complete as soon as the required amount of the appropriate acid has been added, generally from about 10 minutes to about 90 minutes. The product, a 1,2,3-trisubstituted-3-aryl-1-pyrrolinium salt, for example a pyrrolinium perchlorate or a pyrrolinium tetrafluoroborate salt, normally crystallizes out of the reaction mixture as it is formed and can therefore be recovered by filtration of the reaction mixture. The pyrrolinium salt can be used without further purification, or can be recrystallized from a suitable solvent if desired.

The 1,2,3-trisubstituted-3-aryl-1-pyrrolinium salt, with the anion being non-nucleophilic, is treated with diazomethane to provide a bicyclic pyrrolidinium salt. The bicyclic salt is stable, depending upon the nucleophilicity of the anion. For example, the preferred salts, such as the perchlorate, tetraphenylborate, and the tetrafluoroborate salts for example, are stable at temperatures below about 100° C., but decompose at higher temperatures as described hereinbelow.

The reaction between the pyrrolinium salt and diazomethane is preferably carried out in an unreactive organic solvent such as an ether, for example diethyl ether, dipropyl ether, dibutyl ether, tetrahydrofuran, dimethoxyethane; or in an aromatic solvent, examples of which include benzene, toluene, xylene, and the like. Halogenated hydrocarbons such as chloroform, dichloromethane, as well as esters such as ethyl acetate or methyl acetate, are also suitable solvents. The particular solvent selected is not critical to the process. The reaction is generally carried out at a temperature below about 50° C., preferably between about −10° and about 50° C. More specifically, a solution of diazomethane, in diethyl ether for example, can be added to a suspension of the pyrrolinium salt, in diethyl ether or dichloromethane for example, while the temperature of the reaction mixture is maintained at about −10° to about 15° C. After the addition of diazomethane is complete, the temperature of the reaction mixture is preferably allowed to warm to about 20° to 30° C. The amount of diazomethane generally used is at least an equimolar quantity relative to the starting pyrrolinium salt. In practice, it is convenient to use an excess of diazomethane in order to effect complete reaction. The amount of excess diazomethane used is not critical and the reaction can be followed by simply observing the evolution of nitrogen gas. When the gas evolution ceases, enough diazomethane has been added. Alternatively, diazomethane can be added until the reaction solution becomes yellow in color, indicating that a slight excess of diazomethane is present. The reaction is normally complete after about 1 to about 18 hours; however, longer reaction times can be employed if desired. The excess diazomethane in the reaction mixture can be decomposed by the addition of a weak acid, for example acetic acid, or alternatively by evaporation. The product is isolated by removal of the reaction solvent, thereby providing a 1,2,3-trisubstituted-3-aryl-1,2-methylene-pyrrolidinium salt, generally as a crystalline residue. Further purification is normally not needed; however, if desired, the salt can be further purified by recrystallization from a suitable solvent such as, for example, ethyl acetate, chloroform, benzene, ethanol, or the like.

Illustrative examples of novel, 1,2,3-trisubstituted-3-aryl-1,2-methylene-pyrrolidinium salts prepared by the present process include, among others;

1,2-dimethyl-3-ethyl-3-(3-methoxyphenyl)-1,2-methylene-pyrrolidinium perchlorate;
1-n-octyl-2-ethyl-3-n-propyl-3-phenyl-1,2-methylene-pyrrolidinium perchlorate;
1-methyl-2-n-propyl-3-(2-propenyl)-3-(3-methoxyphenyl)-1,2-methylene-pyrrolidinium tetrafluoroborate;
1,2-dimethyl-3-n-butyl-3-(3-ethoxyphenyl)-1,2-methylene-pyrrolidinium tetrafluoroborate;
1,2-diethyl-3-methyl-3-(3-isopropoxyphenyl)-1,2-methylene-pyrrolidinium tetrafluoroborate;
1,2,3-trimethyl-3-(3-methoxyphenyl)-1,2-methylene-pyrrolidinium fluorosulfonate;
1-(2-cyclopropylethyl)-2,3-dimethyl-3-phenyl-1,2-methylene-pyrrolidinium tetrafluoroborate;
1-(cyclobutylmethyl)-2,3-dimethyl-3-phenyl-1,2-methylene-pyrrolidinium tetraphenylborate;
1-(2-methylcyclopropyl)methyl)-2,3-dimethyl-3-phenyl-1,2-methylene-pyrrolidinium fluorosulfonate;
1-benzyl-2,3dimethyl-3-(3-isopropoxyphenyl)-1,2-methylene-pyrrolidinium tetraphenylborate; and
1-(benzyl)-2,3-dimethyl-3-(3-methoxyphenyl)-1,2-methylene-pyrrolidinium tetrafluoroborate.

The 1,2,3-trisubstituted-3-aryl-1,2-methylene-pyrrolidinium salt is heated to a temperature of about 100° to about 250° C., thereby effecting a ring expansion of the bicyclic system and providing a 1,3,4-trisubstituted-4-aryl-1,4,5,6-tetrahydropyridinium salt. The thermal decomposition of the bicyclic ring system can be carried out in any unreactive solvent that has a boiling point above about 100° C. Such solvents include 1,3-dimethoxybenzene, 1,2-dimethylbenzene, 1,2,3-trimethylbenzene, dimethyl sulfoxide, triethylphosphonate, or the like. In general practice, it is preferable to carry out the pyrolysis reaction in the absence of a solvent. In particular, the 1,2,3-trisubstituted-3-aryl-1,2-methylene-pyrrolidinium salt can be heated by itself to a temperature of about 150° to about 225° C. The pyrolysis reaction is substantially complete within about 15 to about 90 minutes. The product is a tetrahydropyridine acid addition salt, for example a hydoperchlorate salt or a hydrotetrafluoroborate salt. The salt can be isolated by crystallization and further purified by recrystallization if desired, but preferably the salt is converted directly to the free tetrahydropyridine by the addition of a suitable base to the pyrolysis reaction mixture. More specifically, the reaction mixture is made alkaline by the addition of an aqueous base such as sodium hydroxide, potassium hydroxide, magnesium hydroxide, ammonium hydroxide, Triton B, or the like. The particular base used is not critical. An organic solvent is generally added to the reaction mixture in order to effect complete solution of the reaction mixture. Typical solvents used to solublize the tetrahydropyridine are, for example, alcohols such as ethanol, methanol, isopropanol, or ethers such as dioxane or tetrahydrofuran. The amount of solvent used is not critical but is generally enough to completely dissolve the tetrahydropyridine. The tetrahydropyridine is extracted from the aqueous alkaline solution into a suitable immiscible organic solvent such as diethyl ether, ethyl acetate, dichloromethane, benzene, or the like. Evaporation of the solvent from the extracts affords a 1,3,4-trisubstituted-4-aryl-1,4,5,6-tetrahydropyridine. The tetrahydropyridine can be used in the next step of the process without further purification, or if desired, the compound can be purified by any of the commonly used methods, for example, distillation, chromatography, crystallization, or the like.

Typical 1,3,4-trisubstituted-4-aryl-1,4,5,6-tetrahydropyridines prepared by the present process are:
1,3,4-trimethyl-4-phenyl-1,4,5,6-tetrahydropyridine;
1,3-dimethyl-4-ethyl-4-(3-methoxyphenyl)-1,4,5,6-tetrahydropyridine;
1-methyl-3-ethyl-4-n-propyl-4-(3-methoxyphenyl)-1,4,5,6-tetrahydroypridine;
1-n-heptyl-3-ethyl-4-(3-butenyl)-4-phenyl-1,4,5,6-tetrahydropyridine;
1-(3-methylheptyl)-3,4-dimethyl-4-phenyl-1,4,5,6-tetrahydropyridine;
1-(cyclobutylmethyl)-3,4-dimethyl-4-phenyl-1,4,5,6-tetrahydropyridine;
1-2-(cyclopropyl)ethyl-3,4-dimethyl-4-phenyl-1,4,5,6-tetrahydropyridine;
1-(cyclohexylmethyl)-3,4-dimethyl-4-(3-methoxyphenyl)-1,4,5,6-tetrahydropyridine;
1-(benzyl)-3,4-dimethyl-4-(3-ethoxyphenyl)-1,4,5,6-tetrahydropyridine;
1-cyclopropylmethyl-3,4-dimethyl-4-(3-methoxyphenyl)-1,4,5,6-tetrahydropyridine;
1-benzyl-3,4-dimethyl-4-phenyl-1,4,5,6-tetrahydropyridine;
1-(benzyl)-3,4-dimethyl-4-(3-methoxyphenyl)-1,4,5,6-tetrahydropyridine; and the like.

It should be noted that in some cases the pyrolysis reaction provides a piperidine, namely, a 3-alkylenepiperidine of the formula

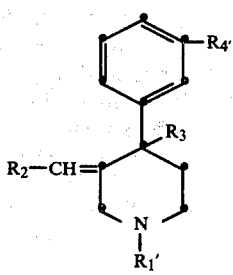

Although the yields of this 3-alkylene-piperidine are generally quite low, isolation can be accomplished if desired, by methods such as chromatography, for example, and the 3-alkylene derivative can be reduced to provide compounds of the invention. Generally, however, the yields are low to the extent that isolation and purification are unwarranted.

The next step of the present process comprises reducing the tetrahydropyridine to provide a 1,3,4-trisubstituted-4-aryl piperidine. The reduction of a 1,4,5,6-tetrahydropyridine can be accomplished by any of a number of methods well known to those skilled in the art. More specifically, the reduction can be accomplished by reaction with hydride reagents such as, for example, sodium borohydride, diborane, lithium aluminum hydride, sodium bis-(2-methoxyethoxy)aluminum hydride, and the like. The hydride reduction reactions are generally carried out in the presence of a suitable solvent, for example in ethers such as diethyl ether, dipropyl ether, tetrahydrofuran, diglyme, or in alcohols such as methanol, ethanol, isopropanol, and the like. Weak acids, such as formic acid or acetic acid for example, can be added to the reaction mixture if desired, thereby making the reduction more efficient. A preferred reduction method, for example, comprises treating a 1,4,5,6-tetrahydropyridine with sodium borohydride in the presence of a suitable solvent, such as tetrahydrofuran, and in the presence of an acid such as, for example, acetic acid. The amount of reducing agent used can vary over a wide range. Generally, the amount of reducing agent used is in excess of the tetrahydropyridine, normally from about 1 to about 10 molar excess; however, more or less can be used if desired. The reaction is usually carried out at a temperature below about 180° C., although the precise temperature is not critical. Preferably, the reactants are mixed while the temperature is maintained at about 0° to about 20° C. After the reactants have been combined, the temperature can be increased, preferably to a temperature from about 50° to about 150° C. Normally, the reduction is complete within about 1 to about 4 hours. The product can be recovered by making the reaction mixture alkaline, for example by adding an aqueous base such as sodium hydroxide, potassium hydroxide, ammonium hydroxide, or the like, and extracting the aqueous alkaline reaction mixture with a water immiscible organic solvent, for example diethyl ether, ethyl acetate, dichloromethane, or the like.

The reduction of a tetrahydropyridine can alternatively be accomplished by hydrogenation. The hydrogenation is preferably carried out in an unreactive solvent such as, for example, tetrahydrofuran, dioxane, ethanol, methanol, water, N,N-dimethylformamide, or the like. The particular solvent used is not critical, but preferably the solvent selected is one in which the tetrahydropyridine will be at lease partially soluble. The hydrogenation is carried out in the presence of a suitable catalyst such as, for example, Raney nickel, platinum oxide, platinum, palladium on a suitable carrier such as carbon or barium sulfate, and the like. The particular reaction conditions are not critical to the process, but generally the hydrogenation is carried out at a temperature of about 25° to about 200° C., with a hydrogen gas pressure of about 20 to about 100 p.s.i. The particular catalyst used in the reaction can determine to some degree the particular piperidine isomer obtained. For example, when platinum oxide is selected as the catalyst, the piperidine product is predominantly in the form of the trans isomer. Alternatively, when the hydrogenation is carried out in the presence of palladium on carbon for example, the piperidine is predominantly the cis isomer. Mixtures of cis and trans 1,3,4-trisubstituted-4-arylpiperidines can be separated, if desired, by any of the commonly used techniques such as, for example, distillation, gas liquid chromatography, solid liquid chromatography, crystallization, and the like.

It should be noted that care must be taken when reducing a 1,4,5,6-tetrahydropyridine when alkenyl substituents are present. Generally, reducing agents that do not normally reduce an isolated carbon-carbon double bond are selected for such a reduction. For example, agents such as sodium borohydride or lithium aluminum hydride are generally preferred.

The 1,3,4-trisubstituted-4-arylpiperidines prepared by the process described hereinabove are valuable pharmacological agents. Some of these piperidines are useful as intermediates in the synthesis of other 1,3,4-trisubstituted-4-arylpiperidines. More specifically, certain of these piperidines can be converted to 3,4-disubstituted-4-arylpiperidines, which compounds are valuable intermediates in preparing compounds of the invention. For example, a 1-methyl-3,4-disubstituted-4-arylpiperidine can be demethylated to provide the corresponding secondary amine. In particular, a 1-methyl-3,4-disubstituted-4-arylpiperidine can be treated with a haloformate to provide a carbamate which gives a secondary amine when treated with a base. This type of reaction is described in more detail by Abdel-Monen and Portoghese, *J. Med. Chem.* 15 208 (1972). In particular a haloformate such as, for example, phenyl chloroformate, ethyl bromoformate, benzyl chloroformate, or the like, is reacted with a tertiary amine, for example a 1-methyl piperidine derivative in the present case, to afford a carbmate. The reaction is generally carried out in an unreactive solvent such as dichloromethane, chloroform, acetone, ethyl acetate, or the like. The temperature is usually held below about 200° C., and the reaction is substantially complete within about 1 to 5 hours. The product carbamate can be isolated by simply evaporating the reaction solvent, and further purification of the product is generally not needed. The carbamate is converted to the 3,4-disubstituted-4-arylpiperidine by the action of a suitable base such as, for example, aqueous sodium hydroxide or aqueous potassium carbonate. A suitable organic solvent is normally added to the reaction mixture in order to dissolve the carbamate. Suitable solvents include alcohols such as ethanol or methanol, or ethers such as dioxane or tetrahydrofuran for example. The hydrolysis reaction is generally complete within about 12 to 36 hours when carried out at a temperature of about 50° to about 150° C. The product is isolated by extracting the aqueous reaction mixture with a suitable solvent such as diethyl ether or ethyl acetate for example. The 3,4-disubstituted-4-arylpiperidine can be further purified by methods such as chromatography, crystallization, distillation, or the like.

The 3,4-disubstituted-4-arylpiperidine can be alkylated at the 1-position to provide any of the compounds of the invention. For example, the piperidine can be alkylated with alkyl halides, alkenyl halides, alkynyl halides, substituted alkyl halides, and the like. Typical examples of alkylating agents include isooctyl iodide, 3-hexenyl bromide, 5-octynyl iodide, cyclopropylmethyl chloride, benzoylethyl bromide, 3-hydroxy-3-phenylpropyl bromide, 3,4-dichlorobenzyl chloride, 4-nitrobenzyl bromide, 3-phenyl-3-propenyl iodide, 3-methyl-4-(methylthio)benzyl iodide, 3-(4-ethoxyphenyl)propyl iodide, phenylthiomethyl iodide, phenoxymethyl iodide, (2-thiophene)methyl iodide, 2-(3-furyl)ethyl iodide, 3-[2-(4-methyl)furyl]propylchloride, and the like.

The desired 1,3,4-trisubstituted-4-arylpiperidine is prepared by reacting a suitable 3,4-disubstituted-4-arylpiperidine with an alkylating agent. The reactants are generally commingled in about equimolar quantities, preferably in an organic solvent. Typical solvents commonly used include amides such as dimethylformamide or dimethylacetamide; sulfoxides such as dimethyl sulfoxide; and the like. Generally, a base is added to the reaction mixture to act as an acid binding agent. Typical bases include sodium bicarbonate, potassium carbonate, magnesium hydroxide, triethylamine, and the like. The alkylation is generally complete after about 1 to about 16 hours when carried out at a temperature of about 20° to 120° C. The products are isolated by general methods and further purified if desired.

Further modification of the 1-substituent can be accomplished if desired. For example, an oxo-group of a 1-substituent can be reduced under general procedures to provide the corresponding hydroxy group, which can then be removed by dehydration if desired.

As indicated hereinbefore, a piperidine with a 3-methoxyphenyl substituent can be converted to the corresponding 3-hydroxyphenyl substituted piperidine. For example, the methoxyl group is converted to the hydroxyl group by treatment with agents such as hydrobromic acid and acetic acid, or boron tribromide for example. Such methods of ether cleavage are well known to those in the art, see for example U.S. Pat. No. 3,324,139. The corresponding 3-hydroxyphenyl substituted piperidine is useful as an analgesic and additionally as an intermediate for preparing other piperidines. For example, the 3-hydroxyphenyl substituent can be acylated with $C_1$–$C_{12}$ alkanoyl groups, or with pyridinoyl groups. Typical acylating agents include acid halides, especially acid bromides and acid chlorides; acid anhydrides, including mixed anhydrides, ketenes, and the like. Examples of typical acylating agents include acetyl chloride, 5-methyloctanoyl iodide, lauryl chloride, 4-pyridinoyl chloride, 3-N-oxopyridinoyl bromide, and the like. The acylation reaction is well known, and is generally carried out in an organic solvent such as acetone, benzene, or chloroform, and in the presence of a base such as sodium bicarbonate, potassium carbonate, or the like.

Salts of piperidines are prepared by methods commonly employed for the preparation of amine salts. In particular, acid addition salts of the piperidines are prepared by reaction of the piperidine with an appropriate acid of pKa less than about 4, generally in an unreactive organic solvent. Suitable acids include mineral acids such as hydrochloric, hydrobromic, hydroiodic, sulfuric, phosphoric, and like acids. Organic acids are also used, for example acetic acid, p-toluenesulfonic acid, chloroacetic acid, and the like. The usual solvents used in the reaction include acetone, tetrahydrofuran, diethyl, ether, ethyl acetate, and the like. Quaternary salts can be prepared in generally the same way by reaction of the piperidine with an alkyl sulfate or alkyl halide, for example, methyl sulfate, methyl iodide, ethyl bromide, propyl iodide, and the like.

When reference is made herein to novel piperidines, it should be understood that the salts are also included. For example, 1,3,4-trialkyl-4-arylpiperidine, when referred to herein, includes the cis isomer, the trans isomer, as well as a mixture of cis and trans isomers thereof, plus the salts of any of these.

Illustrative examples of compounds provided by the present invention are as follows:
1,3,4-trimethyl-4-phenylpiperidine;
1,3-dimethyl-4-ethyl-4-(3-methoxyphenyl)-piperidine;
1,3-dimethyl-4-n-propyl-4-(3-hydroxyphenyl)-piperidine;
1-ethyl-3-methyl-4-n-propyl-4-(3-isopropoxyphenyl)-piperidine;
1-n-propyl-3,4-dimethyl-4-phenylpiperidine;
1-(2-propenyl)-3-methyl-4-(2-propenyl)-4-(3-methoxyphenyl)-piperidine;
1,4-dimethyl-3-(2-propenyl)-4-phenylpiperidine;
1-(2-phenylethyl)-3,4-dimethyl-4-(3-hydroxyphenyl)-piperidine;
1-(3-phenyl-3-hydroxy-n-propyl)-3,4-dimethyl-4-(3-hydroxyphenyl)-piperidine;
1-cyclopropylmethyl-3-methyl-4-n-propyl-4-(3-methoxyphenyl)-piperidine;
1-cyclopentylmethyl-3-ethyl-4-(2-propenyl)-4-(3-ethoxyphenyl)-piperidine;
1-(2-cyclopentylethyl)-3-(3-butenyl)-4-ethyl-4-(3-acetoxyphenyl)-piperidine;
1,3-dimethyl-4-(2-propenyl)-4-(3-methoxyphenyl)-piperidine;
3,4-dimethyl-4-phenylpiperidine;
3-methyl-4-ethyl-4-(3-hydroxyphenyl)-piperidine;
1-benzoylmethyl-3,4-dimethyl-4-(3n-propoxyphenyl)-piperidine;
1-[2-(4-aminophenyl)ethyl]-3,4-dimethyl-4-(3-methoxyphenyl)-piperidine;
1-[2-(4-chlorophenyl)ethyl]-3,4-dimethyl-4-(3-hydroxyphenyl)-piperidine;
1-[3-(4-aminophenyl)-3-hydroxypropyl]-3,4-dimethyl-4-phenylpiperidine;
1-(2-phenylethyl)-3,4-dimethyl-4-phenylpiperidine hydrobromide;
1-n-butyl-3-n-propyl-4-ethyl-4-phenylpiperidine hydrochloride;
1,3-dimethyl-4-ethenyl-4-phenylpiperidine hydroiodide;
1-isopropyl-3-ethyl-4-n-propyl-4-(3-methoxyphenyl)-piperidine hydrobromide;
1-cyclopropylmethyl-3-n-butyl-4-ethyl-4-phenylpiperidine picrate;
1,1-dimethyl-3,4-diethyl-4-phenylpiperidinium iodide;
1,3,4-trimethyl-1-ethyl-4-phenylpiperidinium bromide;
1-(5-methyl-3-hexenyl)3,4-dimethyl-4-(3-[3-pyridinoyloxy]phenyl]-piperidine;
1-(3-phenyl-2-propenyl)-3,4-dimethyl-4-(3-[1-oxo-3-pyridinoyloxy]phenyl)-piperidine;

1-(3,4-dimethylphenoxy)methyl-3,4-dimethyl-4-(3-[4-pyridinoyloxy]phenyl)-piperidine;

1-(3-chloro-4-trifluoromethylphenylthio)methyl-3,4-dimethyl-4-(3-[1-oxo-4-pyridinoyloxy]phenyl)-piperidine;

1-(4-methylthioanilino)methyl-3,4-dimethyl-4-(3-octanoyloxyphenyl)-piperidine;

1-(4-nitro-N-ethylanilino)methyl-3,4-diethyl-4-(3-hydroxyphenyl)-piperidine;

1-(4-trifluoromethyl-N-acetylanilino)methyl-3,4-dimethyl-4-(3-methoxyphenyl)-piperidine;

1-(4-bromobenzoyl)methyl-3-methyl-4-ethyl-4-phenyl-piperidine;

1-(2-phenylthio)ethyl-3,4-dimethyl-4-(3-isopropoxyphenyl)-piperidine;

1-(2-propynyl)-3,4-dimethyl-4-phenyl piperidine; and 1-(5-octynyl)-3,4-dimethyl-4-phenyl piperidine.

In general, the novel piperidines prepared by the present process are valuable compounds for use in human subjects. There is currently a strong need for potent narcotic antagonists for treatment of narcotic abuse. The trans-1,3,4-trisubstituted-4-arylpiperidines of this invention are potent narcotic antagonists which also display analgesia. The cis-1,3,4-trisubstituted-4-arylpiperidines are especially useful as narcotic agonists which produce little physical dependence. The cis compounds are therefore of particular importance in the treatment of pain and suffering. The compounds can be administered either orally or parenterally. For oral administration, they can be formulated in tablets or in a solution or suspension in a suitable carrier, such as water for example. A typical dose which is effective will be from about 0.5 to about 5.0 mg/kg. given from one to about four times each day as needed. For example, an analgesic compound such as cis-1,3-dimethyl-4-n-propyl-4-(3-hydroxyphenyl)piperidine can be formulated and molded into a tablet so that the tablet contains about 200 mg. of active ingredient. Generally, the dose will be determined by the body weight and the individual requirements. When the active ingredient is in the form of such tablet, the tablet can be scored if lower or divided dosages are to be used. Subcutaneous administration can be carried out with the active drug in a suitable carrier, such as an acetone-dispersed suspension in water for example.

The following detailed examples are presented to more fully describe the invention. The examples are illustrative only and are not intended to limit the scope of the invention.

In the examples, the compounds are identified by boiling point or melting point and by elemental analysis.

EXAMPLE 1 trans-1,3,4-Trimethyl-4-phenylpiperidine

A. To a solution of 150 g. of 2,3-dimethyl-3-phenyl-1-pyrroline in 325 cc. of methyl ethyl ketone was added dropwise during ½ hour 94.87 g. of dimethyl sulfate. The reaction mixture was heated at reflux for 2 hours. After the reaction mixture was cooled to about 25° C., 575 cc. of water was added dropwise during ½ hour, and the aqueous reaction mixture was then heated at reflux for 3 hours. The reaction mixture was cooled to about 25° C. and stirred at that temperature for 12 hours. The product was not isolated, but was used as the salt in step B.

B. The reaction mixture from above was made alkaline by the addition of 50 percent aqueous sodium hydroxide until the pH reached about 11. The aqueous alkaline reaction mixture was extracted with diethyl ether. The ethereal extracts were washed with water and dried. Evaporation of the solvent under reduced pressure afforded 160.5 g. of 2-exomethylene-1,3-dimethyl-3-phenylpyrrolidine. B.P. 6674° C. at 0.05 mm/Hg.

C. To a solution of 190 g. of 2-exomethylene-1,3-dimethyl-3-phenylpyrrolidine in 4000 cc. of diethyl ether was added a 50 percent solution of tetrafluoroboric acid in ethyl alcohol until the ethereal solution was acidic when tested with congo red indicator paper. The 1,2,3-trimethyl-3-phenyl-1-pyrrolinium tetrafluoroborate crystallized and was collected by filtration and dried. M.P. 143°–144° C.

Analysis Calc. for $C_{13}H_{18}NBF_4$ (percent): C, 56.75; H, 6.60; N, 5.09. Found: (percent) C, 57.79; H, 6.80; N, 5.79.

D. A solution of 17 g. of 1,2,3-trimethyl-3-phenyl-1-pyrrolinium tetrafluoroborate in 400 cc. of dichloromethane was stirred and cooled to 0° C. in an ice-water bath. A solution of diazomethane in diethyl ether was added dropwise to the reaction mixture over 2½ hours. The reaction mixture was warmed to 25° C. and stirred for 12 hours. The solvent was evaporated from the reaction mixture under reduced pressure to provide 1,2,3-trimethyl-3-phenyl-1,2-methylene pyrrolidinium tetrafluoroborate as a solid. M.P. 151°–155° C.

Analysis Calc. for $C_{14}H_{20}NBF_4$ (percent) C, 58.15; H, 6.97; N, 4.84. Found (percent) C, 58.02; H, 7.12; N, 5.01.

Additional 1,2,3-trisubstituted-3-aryl-1,2-methylene pyrrolidinium tetrafluoroborates prepared according to steps A, B, C, and D above are as follows:

1,2-dimethyl-3-ethyl-3-phenyl-1,2-methylenepyrrolidinium tetrafluoroborate.

Analysis Calc. for $C_{15}H_{22}NBF_4$ (percent): C, 59.42; H, 7.32; N, 4.62. Found (percent) C, 59.23; H, 7.48; N, 4.37.

1,2,3-trimethyl-3-(3-methoxyphenyl)-1,2-methylene pyrrolidinium tetrafluoroborate. M.P. 98°–101° C.

Analysis Calc. for $C_{15}H_{22}NOBF_4$ (percent): C, 56.45; H, 6.95; N, 4.39. Found (percent) C, 56.17; H, 7.14; N, 4.39.

1,2-dimethyl-3-n-propyl-3-(3-methoxyphenyl)-1,2-methylene-pyrrolidinium tetrafluoroborate. M.P. 121°–124° C.

Analysis Calc. for $C_{17}H_{26}NOBF_4$ (percent): C, 58.80; H, 7.55; N, 4.03. Found (percent) C, 58.77; H, 7.69; N, 4.21.

E. 1,2,3-Trimethyl3-phenyl-1,2-methylene-pyrrolidinium tetrafluoroborate was heated at 180° C. for 45 minutes in an oil bath. The crystalline residue was 1,3,4-trimethyl-4-phenyl-1,4,5,6-tetrahydropyridinium tetrafluoroborate.

f. The crystalline residue from above was dissolved in ethyl alcohol and 20 percent aqueous sodium hydroxide was added to the reaction mixture until the mixture was alkaline. The aqueous reaction mixture was extracted with diethyl ether. The ethereal extracts were washed with water and dried. Evaporation of the solvent under reduced pressure afforded 1,3,4-trimethyl-4-phenyl-1,4,5,6-tetrahydropyridine as an oil. B.P. 76°–80° C. at 0.5 mm/Hg.

Analysis Calc. for $C_{14}H_{19}N$ (percent): C, 83.53; H, 9.51; N, 6.96. Found (percent) C, 83.47; H, 9.42; N, 6.74.

Additional 1,3,4-trisubstituted-4-aryl-1,4,5,6-tetrahydropyridines prepared according to the foregoing procedure are as follows:

1,3-dimethyl-4-n-propyl-4-phenyl-1,4,5,6-tetrahydropyridine. B.P. 90°–95° C. at 0.15 mm/Hg.

Analysis Calc. for $C_{16}H_{23}N$ (percent): C, 83.79; H, 10.11; N, 6.11. Found (percent) C, 83.86; H, 9.86; N, 5.93.

1,3-dimethyl-4-ethyl-4-(3-methoxyphenyl)-1,4,5,6-tetrahydropyridine. B.P. 118°–125° C. at 0.1 mm/Hg.

Analysis Calc. for $C_{16}H_{23}NO$ (percent) C, 78.32; H, 9.45; N, 5.71. Found (percent) C, 78.10; H, 9.24; N, 5.72.

1,3-dimethyl-4-n-propyl-4-(3-methoxyphenyl)-1,4,5,6-tetrahydropyridine. B.P. 124°–135° C. at 0.1 mm/Hg.

Analysis Calc. for $C_{17}H_{25}NO$ (percent): C, 78.72; H, 9.71; N, 5.40. Found (percent) C, 78.48; H, 9.80; N, 5.43.

G. A solution of 50 g. of 1,3,4-trimethyl-4-phenyl-1,4,5,6-tetrahydropyridine in 2600 cc. of tetrahydrofuran containing 38 g. of sodium borohydride was stirred and cooled to 5° C. in an ice-water bath. To the reaction mixture was added 578 cc. of glacial acetic acid at a rate such as to maintain the temperature of the reaction mixture between 5° C. and 10° C. After the addition was complete, the reaction mixture was stirred at 10° C. for ½ hour and then heated at reflux for 1 hour. The reaction mixture was cooled to about 25° C. and 25 percent aqueous sodium hydroxide was added to adjust the pH to 11.5. The alkaline reaction mixture was extracted with diethyl ether. The ethereal extracts were washed with water and dried over sodium sulfate. After filtering the drying agent, the solvent was evaporated under reduced pressure to provide 47 g. of essentially pure trans-1,3,4-trimethyl-4-phenylpiperidine. B.P. 90°–92° C. at 0.15 mm/Hg.

Analysis Calc. for $C_{14}H_{21}N$ (percent) C, 82.70; H, 10.41; N, 6.89. Found (percent) C, 82.47; H, 10.11; N, 7.03.

EXAMPLE 2 trans-1,3,4-Trimethyl-4-phenylpiperidine hydrobromide

A solution of 42 g. of 1,3,4-trimethyl-4-phenyl-1,4,5,6-tetrahydropyridine in 450 cc. of ethyl alcohol containing 4.0 g. of platinum oxide was stirred at room temperature for 16 hours under hydrogen gas atmosphere of 50 p.s.i. The reaction mixture was filtered and the filtrate was evaporated to dryness under reduced pressure. The residual oil was dissolved in diethyl ether and gaseous hydrogen bromide was added to the solution. The crystalline salt was collected by filtration and recrystallized from 100 cc. of isopropyl ether, 300 cc. of isopropyl alcohol, and 350 cc. of ethyl alcohol. The product was collected by filtration and dried, providing 31.3 g. of 80 percent pure trans-1,3,4-trimethyl-4-phenylpiperidine hydrobromide. M.P. 242°–245° C.

Analysis Calc. for $C_{14}H_{22}NBr$ (percent): C, 59.16; H, 7.80; N, 4.93. Found (percent) C, 59.29; H, 8.06; N, 5.09.

EXAMPLE 3 cis-1,3,4-Trimethyl-4-phenylpiperidine

A solution of 56.0 g. of 1,3,4-trimethyl-4-phenyl-1,4,5,6-tetrahydropyridine in 900 cc. of glacial acetic acid containing 3.6 g. of 5 percent palladium on carbon was stirred at room temperature for 4 hours under a hydrogen atmosphere of 50 p.s.i. The reaction mixture was diluted with 400 cc. of water and concentrated under reduced pressure. The concentrated reaction mixture was made alkaline by the addition of aqueous sodium hydroxide. The aqueous alkaline solution was extracted with diethyl ether, and the ethereal extracts were washed with water and dried. Evaporation of the solvent under reduced pressure provided cis-1,3,4-trimethyl-4-phenylpiperidine, which was converted to the hydrobromide salt by reaction with hydrogen bromide. M.P. 230°–232° C.

Analysis Calc. for $C_{14}H_{22}NBr$ (percent): C, 59.16; H, 7.80; N, 4.93. Found (percent) C, 59.34; H, 7.59; N, 5.09.

EXAMPLE 4 cis-1,3-Dimethyl-4-n-propyl-4-(3-methoxyphenyl)-piperidine

Following the method of Example 1, 1,3-dimethyl-4-n-propyl-4-(3-methoxyphenyl)-1,4,5,6-tetrahydropyridine was prepared from the corresponding 2-methyl-3-n-propyl-3-(3-methoxyphenyl)-1-pyrroline.

A solution of 81 g. of 1,3 dimethyl-4-n-propyl-4-(3-methoxyphenyl)-1,4,5,6-tetrahydropyridine in 650 cc. of ethyl alcohol containing 8.0 g. of 5 percent palladium suspended on carbon was stirred at room temperature for 16 hours under a hydrogen gas atmosphere of 50 p.s.i. The reaction mixture was filtered, and the filtrate was evaporated under reduced pressure to provide the product as an oil. The hydrobromide salt was prepared in the manner of Example 2 to provide 44 g. of cis-1,3-dimethyl-4-n-propyl-4-(3-methoxyphenyl)-piperidine hydrobromide. M.P. 167°–169.5° C.

Analysis Calc. for $C_{17}H_{28}NOBr$ (percent): C, 59.65; H, 8.24; N, 4.09. Found (percent) C, 59.88; H, 8.46; N, 4.00.

EXAMPLE 5 trans-3,4-Dimethyl-4-phenylpiperidine

To a solution of 32.3 g. of trans-1,3,4-trimethyl-4-phenylpiperidine in 300 cc. of dichloromethane was added a solution of phenyl chloroformate in 75 cc. of dichloromethane. The reaction mixture was stirred at ambient temperature for 10 hours and then heated at reflux for 2 hours. The reaction solution was evaporated to dryness under reduced pressure and the residue was added to 360 cc. of 50 percent aqueous potassium hydroxide and 2000 cc. of ethanol, and diluted with 1450 cc. of water. The alkaline reaction mixture was heated at reflux for 24 hours. The reaction mixture was extracted with diethyl ether and the combined ethereal extracts were washed with water and dried. The solvent was evaporated from the extracts under reduced pressure to provide 23 g. of trans-3,4-dimethyl-4-phenylpiperidine. B.P. 78°–84° C. at 1.5 mm/Hg.

Analysis Calc. for $C_{13}H_{19}N$ (percent): C, 82.48; H, 10.12; N, 7.40. Found (percent) C, 82.60; H, 10.34; N, 7.59.

EXAMPLES 6–11

The following 3,4-disubstituted-4-arylpiperidines were prepared by the method of Example 5, from the corresponding 1,3,4-trisubstituted-4-arylpiperidines.

cis-3-methyl-4-ethyl-4-phenylpiperidine.

Analysis Calc. for $C_{14}H_{21}N$ (percent): C, 82.70; H, 10.41; N, 6.89. Found (percent) C, 82.88; H, 10.11; N, 6.81.

cis-3-methyl-4-n-propyl-4-phenylpiperidine

Analysis Calc. for $C_{15}H_{23}N$ (percent): C, 82.89; H, 10.67; N, 6.44. Found (percent) C, 82.84; H, 10.42; N, 6.24.

trans-3-methyl-4-ethyl-4-phenylpiperidine. B.P. 100°–105° C. at 4 mm/Hg.

Analysis Calc. for $C_{14}H_{21}N$ (percent): C, 82.70; H, 10.41; H, 6.89. Found (percent) C, 82.48; H, 10.23; N, 7.15.

trans-3-methyl-4-n-propyl-4-phenylpiperidine. B.P. 133°–140° C. at 5 mm/Hg.

Analysis Calc. for $C_{15}H_{23}N$ (percent): C, 82.89; H, 10.67; N, 6.44. Found (percent) C, 82.91; H, 10.61; N, 6.15.

trans-3,4-dimethyl-4-(3-methoxyphenyl)-piperidine. B.P. 150°–155° C. at 3 mm/Hg.

Analysis Calc. for $C_{14}H_{21}NO$ (percent): C, 76.67; H, 9.65; N, 6.39. Found (percent) C, 76.92; H, 9.91; N, 6.61.

trans-3-methyl-4-ethyl-4-(3-methoxyphenyl)-piperidine. B.P. 145°–150° C. at 5 mm/Hg.

Analysis Calc. for $C_{15}H_{20}NO$ (percent): C, 77.21; H, 9.94; N, 6.00. Found (percent) C, 77.26; H, 9.71; N, 5.75.

EXAMPLE 12 cis-1-Ethyl-3,4-dimethyl-4-phenylpiperidine

To a solution of 1.5 g. of cis-3,4-dimethyl-4-phenylpiperidine in 24 cc. of dimethylformamide containing 0.96 g. of sodium bicarbonate was added 1.14 g. of ethyl iodide. The reaction mixture was heated at reflux for 1 hour. After cooling the reaction mixture to about 25° C., 250 cc. of water was added and the aqueous reaction mixture was extracted with diethyl ether. The ethereal extracts were washed with water and dried. Evaporation of the solvent under reduced pressure afforded 1.6 g. of 1-ethyl-3,4-dimethyl-4-phenylpiperidine as an oil. The oil was dissolved in diethyl ether and hydrogen bromide gas was added to the ethereal solution, thereby affording crystals which were collected by filtration. Recrystallization from 100 cc. of isopropyl alcohol and 30 cc. of isopropyl ether afforded 1.61 g. of cis-1-ethyl-3,4-dimethyl-4-phenylpiperidine hydrobromide. M.P. 224°–226° C.

Analysis Calc. for $C_{15}H_{24}NBr$ (percent): C, 60.40; H, 8.11; N, 4.70. Found (percent) C, 60.64; H, 7.83; N, 4.97.

EXAMPLES 13–22

The following compounds were prepared by the method of Example 12, from the corresponding 3,4-disubstituted-4-arylpiperidine and the appropriate alkylating agent.

trans-1-n-propyl-3,4-dimethyl-4-phenylpiperidine hydrobromide. M.P. 214.5°–217° C.

Analysis Calc. for $C_{16}H_{26}NBr$ (percent): C, 61.54; H, 8.39; N, 4.49. Found (percent) C, 61.57; H, 8.56; N, 4.54.

trans-1-(2-propenyl)-3,4-dimethyl-4-phenylpiperidine hydrobromide. M.P. 194°–195° C.

Analysis Calc. for $C_{16}H_{24}NBr$ (percent): C, 61.94; H, 7.80; N, 4.51. Found (percent) C, 62.20; H, 8.05; N, 4.63.

trans-1-cyclopropylmethyl-3,4-dimethyl-4-phenylpiperidine hydrobromide, M.P. 197°–199° C.

Analysis Calc. for $C_{17}H_{26}NBr$ (percent): C, 62.96; H, 8.08; N, 4.32. Found (percent) C, 62.83; H, 8.30; N, 4.47.

trans-1-[2-(4-nitrophenyl)ethyl]-3,4-dimethyl-4-phenylpiperidine hydrochloride. M.P. 225°–228° C.

Analysis Calc. for $C_{21}H_{27}N_2O_2Cl$ (percent): C, 67.28; H, 7.26; N, 7.47. Found (percent) C, 67.07; H, 7.38; N, 7.75.

trans-1-[2-(4-hydroxyphenyl)ethyl]-3,4-dimethyl-4-phenylpiperidine hydrobromide M.P. 253°–255° C.

Analysis Calc. for $C_{21}H_{28}NOBr$ (percent): C, 64.61; H, 7.23; N, 3.59. Found (percent) C, 64.36; H, 7.29; N, 3.46.

trans-(2-propenyl)-3,4-dimethyl-4-(3-methoxyphenyl)piperidine hydrobromide, M.P. 145°–147° C.

Analysis Calc. for $C_{17}H_{26}NOBr$ (percent): C, 60.00; H, 7.78; N, 4.12. Found (percent) C, 59.81; H, 7.96; N, 4.08.

trans-1-cyclopropylmethyl-3,4-dimethyl-4-(3-methoxyphenyl)piperidine hydrochloride. M.P. 186°–188° C.

Analysis Calc. for $C_{18}H_{28}NOCl$ (percent): C, 69.77; H, 9.11; N, 4.52. Found (percent) C, 69.54; H, 8.95; N, 4.75.

cis-1-(2-propenyl)-3,4-dimethyl-4-phenylpiperidine hydrobromide. M.P. 195°–197° C.

Analysis Calc. for $C_{16}H_{24}NBr$ (percent): C, 61.94; H, 7.80; N, 4.51. Found (percent) C, 61.66; H, 7.53; N, 4.76.

cis-1-cyclobutylmethyl-3,4-dimethyl-4-phenylpiperidine hydrobromide. M.P. 250°–252° C.

Analysis Calc. for $C_{18}H_{28}NBr$ (percent): C, 63.90; H, 8.34; N, 4.14. Found (percent) C, 64.09; H, 8.38; N, 4.34.

EXAMPLE 23 trans-1-Phenylacetyl-3,4-dimethyl-4-phenylpiperidine

To a cooled solution of 4.0 g. of trans-3,4-dimethyl-4-phenylpiperidine in 75 cc. of methanol containing 4.2 g. of potassium carbonate and 22 cc. of water was added 4.2 g. of phenylacetyl chloride dropwise so as to maintain the reaction temperature at about 5° to 10° C. The reaction mixture was stirred at 5° to 10° C. for ½ hour after the addition was complete, and then the reaction mixture was stirred at about 24° C. for 15 hours. The reaction solvent was evaporated under reduced pressure to give a residue which was then dissolved in diethyl ether. The ethereal solution was washed first with dilute aqueous sodium bicarbonate, then with dilute aqueous hydrochloric acid, and finally with water. After drying the ethereal solution over potassium carbonate and filtering the drying agent, the solvent was removed under reduced pressure to provide 4.3 g. of trans-1-phenylacetyl-3,4-dimethyl-4-phenylpiperidine.

EXAMPLE 24 trans-1-(2-phenylethyl)-3,4-dimethyl-4-phenylpiperidine

A solution of trans-1-phenylacetyl-3,4-dimethyl-4-phenylpiperidine in 25 cc. of tetrahydrofuran was added dropwise to a solution of 3.2 g. of lithium aluminum hydride in 150 cc. of tetrahydrofuran. The reaction mixture was heated at reflux for 4 hours. After being cooled, the reaction mixture was added to 30 cc. of water containing 6 cc. of 20 percent aqueous sodium hydroxide. The aqueous alkaline reaction mixture was extracted with diethyl ether. The ethereal extracts were washed with water and dried. Evaporation of the solvent under reduced pressure afforded 4.0 g. of the product as an oil. The oil was dissolved in diethyl ether and gaseous hydrogen bromide was added to the ethereal solution to provide 2.8 g. of trans-1-(2-phenylethyl)-3,4-dimethyl-4-phenylpiperidine hydrobromide. M.P. 256°–258° C.

Analysis Calc. for $C_{21}H_{28}NBr$ (percent): C, 67.38; H, 7.54; N, 3.74. Found (percent) C, 67.68; H, 7.81; N, 3.81.

EXAMPLES 25–27

The following compounds were prepared by the method of Example 24, from the corresponding substituted piperidine.

trans-1-[2-(4-methoxyphenyl)ethyl]-3,4-dimethyl-4-phenylpiperidine hydrobromide. M.P. 265° C. dec.

Analysis Calc. for $C_{22}H_{30}NOBr$ C, 65.34; H, 7.48; N, 3.46. Found (percent) C, 65.57; H, 7.38; N, 3.57.

trans-1-[2-(4-hydroxyphenyl)ethyl]-3,4-dimethyl-4-phenylpiperidine hydrobromide. M.P. 253°-255° C.

Analysis Calc. for $C_{21}H_{28}NOBr$ (percent): C, 64.61; H, 7.23; N, 3.59. Found (percent) C, 64.36; H, 7.29; N, 3.46.

trans-1-(2-phenylethyl)-3,4-dimethyl-4-(3-methoxyphenyl)piperidine hydrobromide. M.P. 229°-231° C.

Analysis Calc. for $C_{22}H_{30}NOBr$ (percent): C, 65.34; H, 7.48; N, 3.46. Found (percent) C, 65.29; H, 7.32; N, 3.44.

EXAMPLE 28 trans-1-(2-benzoylethyl)-3,4-dimethyl-4-phenylpiperidine

To a solution of 3.0 g. of trans-3,4-dimethyl-4-phenylpiperidine in 25 cc. of dimethylformamide containing 3.26 g. of sodium carbonate was added 5.42 g. of (2-benzoylethyl)-trimethylammonium iodide. The reaction mixture was stirred at 25° C. for 5 hours under a nitrogen atmosphere. After diluting the reaction mixture with 200 cc. of water, the mixture was extracted with diethyl ether. The ethereal extracts were combined and washed with water and dried over potassium carbonate. The drying agent was filtered and the filtrate was evaporated to dryness under reduced pressure, affording 5.0 g. of the product as an oil. The oil was dissolved in diethyl ether and gaseous hydrogen bromide was added to precipitate the hydrobromide salt, which was collected by filtration and recrystallized from 100 cc. of isopropyl alcohol to give 5.05 g. of trans-1-(2-benzoylethyl)-3,4-dimethyl-4-phenylpiperidine hydrobromide. M.P. 200°-203° C.

Analysis Calc. for $C_{22}H_{28}NOBr$ (percent): C, 65.67; H, 7.01; N, 3.48. Found (percent) C, 65.60; H, 7.03; N, 3.46.

EXAMPLE 29

The following compound was prepared by the method of Example 28.

cis-1-(2-benzoylethyl)-3,4-dimethyl-4-phenylpiperidine hydrobromide. M.P. 204°-206° C.

Analysis Calc. for $C_{22}H_{28}NOBr$ (percent): C, 65.67; H, 7.01; N, 3.48. Found (percent) C, 65.45; H, 6.80; N, 3.59.

EXAMPLE 30 trans-1-(2-phenylethyl)-3,4-dimethyl-4-(3-hydroxyphenyl)piperidine

A solution of 9.2 g. of trans-1-(2-phenylethyl)-3,4-dimethyl-4-(3-methoxyphenyl)piperidine in 100 cc of acetic acid containing 100 cc. of 48 percent aqueous hydrobromic acid was heated at reflux for 4 hours. After the reaction mixture was cooled to about 25° C., 200 cc. of water was added, and the aqueous mixture was made basic by the addition of ammonium hydroxide. The alkaline mixture was extracted with ethyl acetate, and the organic extracts were combined and washed with water and dried. Evaporation of the solvent provided the product as an oil. The oil was dissolved in diethyl ether, and gaseous hydrochloric acid was added, thereby affording trans-1-(2-phenylethyl)-3,4-dimethyl-4-(3-hydroxyphenyl)piperidine hydrochloride as white crystals which were filtered and dried. M.P. 166°-170° C.

Analysis Calc. for $C_{21}H_{28}NOCl$ (percent): C, 72.92; H, 8.16; N, 4.05. Found (percent) C, 73.07; H, 8.25; N, 4.02.

EXAMPLES 31-34

The following compounds were prepared by the method of Example 30, from the corresponding 1,3,4-trisubstituted-4-(3-methoxyphenyl)piperidine.

cis-1,3-dimethyl-4-ethyl-4-(3-hydroxyphenyl)piperidine hydrobromide. M.P. 228°-232° C.

Analysis Calc. for $C_{15}H_{24}NOBr$ (percent): C, 57.33; H, 7.70; N, 4.46. Found (percent) C, 57.54; H, 7.53; N, 4.24.

trans-1-cyclopropylmethyl-3,4-dimethyl-4-(3-hydroxyphenyl)piperidine hydrochloride. M.P. 179°-181° C.

Analysis Calc. for $C_{17}H_{26}NOCl$ (percent): C, 69.02; H, 8.86; N, 4.73. Found (percent) C, 68.80; H, 9.07; N, 4.99.

trans-1,3,4-trimethyl-4-(3-hydroxyphenyl)piperidine hydrochloride. M.P. 185°-187° C.

Analysis Calc. for $C_{14}H_{22}NOCl$ (percent): C, 65.74; H, 8.67; N, 5.48. Found (percent) C, 65.73; H, 8.69; N, 5.35.

trans-3,4-dimethyl-4-(3-hydroxyphenyl)piperidine. M.P. 159°-164° C.

Analysis Calc. for $C_{13}H_{19}NO$ (percent): C, 76.06; H, 9.33; N, 6.82. Found (percent) C, 75.87; H, 9.23; N, 6.86.

EXAMPLE 35 cis-1-(3-phenyl-3-hydroxypropyl)-3,4-dimethyl-4-phenylpiperidine

A solution of cis-1-(2-benzoylethyl)-3,4-dimethyl-4-phenylpiperidine in 20 cc. of dry benzene was added dropwise to a stirred solution of lithium bis(2-methoxyethoxy)aluminum hydride at a rate such as to maintain the temperature between 25° and about 45° C. After the addition was complete, the reaction mixture was heated at reflux for 2½ hours. Stirring was continued for 12 hours after the reaction mixture was cooled to about 25° C. The reaction mixture was made alkaline by the addition of 50 cc. of 1 N sodium hydroxide, and the aqueous alkaline reaction mixture was extracted with diethyl ether. The ethereal extracts were washed with water and dried and the solvent was removed under reduced pressure, affording cis-1-(3-phenyl-3-hydroxypropyl)-3,4-dimethyl-4-phenylpiperidine. The hydrochloride salt was prepared in the usual manner. M.P. 144°-149° C.

Analysis Calc. for $C_{22}H_{30}NOCl$ (percent): C, 73.41; H, 8.40; N, 3.89. Found (percent) C, 73.64; H, 8.55; N, 3.95.

EXAMPLES 36-50

The following compounds were prepared by the methods of Examples 1, 5, 12, 24, and 31.

trans-1-(2-propenyl)-3-methyl-4-ethyl-4-phenylpiperidine hydrobromide. M.P. 200°-203° C.

Analysis Calc. for $C_{17}H_{26}NBr$ (percent): C, 62.96; H, 8.08; N, 4.32. Found (percent) C, 62.90; H, 7.99; N, 4.17.

trans-1-cyclopropylmethyl-3-methyl-4-ethyl-4-phenylpiperidine hydrobromide. M.P. 228°-230° C.

Analysis Calc. for $C_{18}H_{28}NBr$ (percent): C, 63.90; H, 8.34; N, 4.14. Found (percent) C, 63.65; H, 8.50; N, 4.35.

trans-1-(2-phenylethyl)-3-methyl-4-ethyl-4-phenyl-piperidine hydrobromide. M.P. 275° C. dec.

Analysis Calc. for $C_{22}H_{30}NBr$ (percent): C, 68.03; H, 7.79; N, 3.61. Found (percent) C, 68.01; H, 8.01; N, 3.32.

cis-1-cyclopropylmethyl-3-methyl-4-ethyl-4-phenyl-piperidine hydrobromide. M.P. 193°–195° C.

Analysis Calc. for $C_{18}H_{29}NBr$ (percent): C, 63.90; H, 8.34; N, 4.14. Found (percent) C, 64.17; H, 8.43; N, 4.13.

cis-1,3-dimethyl-4-ethyl-4-(3-methoxyphenyl)piperidine picrate. M.P. 130°–135° C.

Analysis Calc. for $C_{22}H_{28}N_4O_8$ (percent): C, 55.46; H, 5.92; N, 11.76. Found (percent) C, 55.26; H, 6.14; N, 11.67.

trans-1,3-dimethyl-4-n-propyl-4-phenylpiperidine hydrobromide. M.P. 254°–257° C.

Analysis Calc. for $C_{16}H_{26}NBr$ (percent): C, 61.54; H, 8.39; N, 4.49. Found (percent) C, 61.61; H, 8.16; N, 4.38.

trans-1-(2-propenyl)-3-methyl-4-n-propyl-4-phenyl-piperidine hydrobromide. M.P. 179°–181° C.

Analysis Calc. for $C_{18}H_{28}NBr$ (percent): C, 63.90; H, 8.34; N, 4.14. Found (percent) C, 63.81; H, 8.51; N, 4.30.

trans-1,3-dimethyl-4-n-propyl-4-(3-methoxyphenyl)-piperidine hydrobromide. M.P. 222°–229° C.

Analysis Calc. for $C_{17}H_{28}NOBr$ (percent): C, 59.65; H, 8.24; N, 4.09. Found (percent) C, 59.82; H, 7.94; N, 4.29.

trans-1,3-dimethyl-4-n-propyl-4-(3-hydroxyphenyl)-piperidine hydrobromide. M.P. 261°–262° C.

Analysis Calc. for $C_{16}H_{26}NOBr$ (percent): C, 58.54; H, 7.98; N, 4.27. Found (percent) C, 58.28; H, 7.71; N, 4.04.

trans-1-(2-phenylethyl)-3-methyl-4-n-propyl-4-(3-hydroxyphenyl)piperidine hydrobromide. M.P. 124°–128° C.

Analysis Calc. for $C_{23}H_{32}NOBr$ (percent): C, 66.02; H, 7.71; N, 3.35. Found (percent) C, 66.24; H, 7.70; N, 3.06.

cis-1-cyclopropylmethyl-3-methyl-4-n-propyl-4-phenylpiperidine hydrobromide. M.P. 217°–221° C.

Analysis Calc. for $C_{19}H_{30}NBr$ (percent): C, 64.77; H, 8.58; N, 3.98. Found (percent) C, 64.48; H, 8.45; N, 3.84 cis-1,3-dimethyl-4-n-propyl-4-(3-methoxyphenyl)-piperidine hydrobromide. M.P. 167°–169.5° C.

Analysis Calc. for $C_{17}H_{28}NOBr$ (percent): C, 59.65; H, 8.24; N, 4.09. Found (percent) C, 59.88; H, 8.46; N, 4.00.

cis-1-(2-propenyl)-3-methyl-4-n-propyl-4-(3-methoxyphenyl)piperidine hydrobromide. M.P. 184°–196° C.

Analysis Calc. for $C_{19}H_{30}NOBr$ (percent): C, 61.95; H, 8.21; N, 3.80. Found (percent) C, 61.92; H, 7.96; N, 3.61.

cis-1,3-dimethyl-4-n-propyl-4-(3-hydroxyphenyl)-piperidine hydrobromide. M.P. 222°–224° C.

Analysis Calc. for $C_{16}H_{26}NOBr$ (percent): C, 58.54; H, 7.98; N, 4.20. Found (percent) C, 58.83; H, 8.09; N, 4.02.

cis-1-(2-phenylethyl)-3-methyl-4-n-propyl-4-(3-hydroxyphenyl)piperidine. M.P. 182°–184° C.

Analysis Calc. for $C_{23}H_{31}NO$ (percent): C, 81.85; H, 9.26; N, 4.15. Found (percent) C, 82.12; H, 9.32; N, 4.04.

EXAMPLE 51

The following formulation is suitable for the oral treatment of pain according to the method of this invention.

| Ingredient | Amount |
|---|---|
| cis-1,3-dimethyl-4-n-propyl 4-(3-hydroxyphenyl)piperidine hydrobromide | 200 mg |
| starch powder | 150 mg |
| lactose | 150 mg |
| | 500 mg |

EXAMPLE 52

The following formulation is suitable for the oral treatment of narcotic addiction according to the method of this invention.

| Ingredient | Amount |
|---|---|
| trans-1-(2-benzoylethyl)-3,4-dimethyl-4-(3-hydroxyphenyl)piperidine | 300 mg |
| starch powder | 100 mg |
| lactose | 100 mg |
| | 500 mg |

I claim:

1. A method of treating narcotic addition which comprises administering to a human an effective dose of a compound having the formula

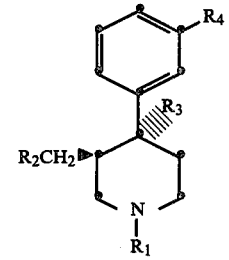

wherein: $R_1$ is $C_1$–$C_8$ alkyl, $C_4$–$C_8$ (cycloalkyl)alkyl, benzyl, $C_3$–$C_8$ alkenyl, $C_3$–$C_8$ alkynyl or

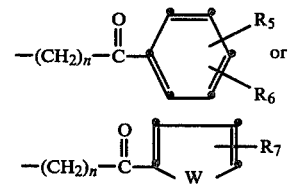

wherein:
n is 1, 2, or 3;
W is O or S;
$R_5$ is $C_1$–$C_3$ alkylthio, nitro, amino, trifluoromethyl, hydroxy, or $R_6$;
$R_6$ is hydrogen, $C_1$–$C_3$ alkyl, $C_1$–$C_3$ alkoxy, or halogen;
$R_7$ is hydrogen or methyl;
$R_2$ is hydrogen, $C_1$–$C_4$ alkyl, or $C_2$–$C_6$ alkenyl;
$R_3$ is $C_1$–$C_4$ alkyl or $C_2$–$C_6$ alkenyl; and
$R_4$ is hydrogen, hydroxy, $C_1$–$C_3$ alkoxy; $C_1$–$C_{12}$ alkanoyloxy or

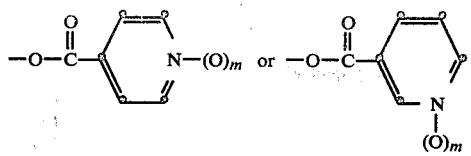

in which m is 0 or 1.

2. The method of claim 1 wherein in the compound administered, $R_1$ is

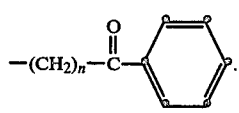

3. The method of claim 2 wherein in the compound administered, $R_2$ is hydrogen and $R_3$ is $C_1$-$C_4$ alkyl.

4. The method of claim 3 wherein in the compound administered, $R_4$ is hydroxy.

5. The method of claim 4 wherein the compound administered is trans-1-(2-benzoylethyl)-3,4-dimethyl-4-(3-hydroxyphenyl)piperidine.

6. A method of producing analgesia comprising administering to a human an analgesically effective dose of a compound of the formula

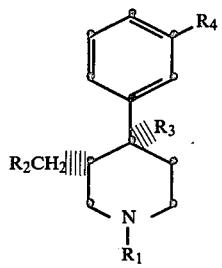

wherein: $R_1$ is $C_1$-$C_8$ alkyl, $C_3$-$C_8$ alkenyl, $C_3$-$C_8$ alkynyl, $C_4$-$C_8$ (cycloalkyl)alkyl,

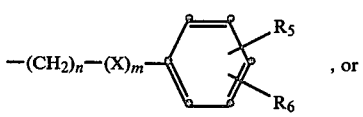, or

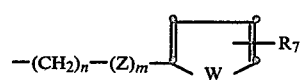

wherein:
n is 1, 2, or 3;
m is 0 or 1;
X is

$CH=CH$, S, O or $NR_8$,
wherein: $R_8$ is hydrogen, $C_1$-$C_4$ alkyl or $C_1$-$C_4$ alkanoyl,
Z is

or $CH=CH$
W is O or S;
$R_5$ is $C_1$-$C_3$ alkylthio, nitro, amino, trifluoromethyl, hydroxy, or $R_6$;
$R_6$ is hydrogen, $C_1$-$C_3$ alkyl, $C_1$-$C_3$ alkoxy, or halogen;
$R_7$ is hydrogen or methyl;
$R_2$ is hydrogen, $C_1$-$C_4$ alkyl, or $C_2$-$C_6$ alkenyl;
$R_3$ is $C_1$-$C_4$ alkyl or $C_2$-$C_6$ alkenyl; and
$R_4$ is hydrogen, hydroxy, $C_1$-$C_3$ alkoxy, $C_1$-$C_{12}$ alkanoyloxy, or

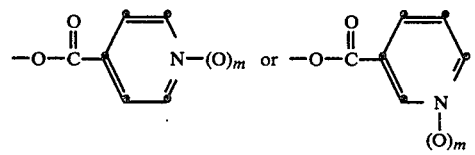

and the pharmaceutically acceptable salts thereof.

7. The method of claim 6 wherein the compound administered has the formula

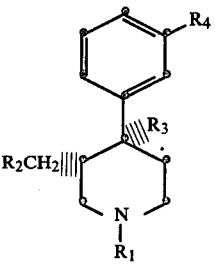

wherein:
$R_1$ is $C_1$-$C_8$ alkyl or $C_4$-$C_8$ (cycloalkyl) alkyl;
$R_2$ is hydrogen or $C_1$-$C_4$ alkyl;
$R_3$ is $C_1$-$C_4$ alkyl;
$R_4$ is hydrogen, hydroxy, or $C_1$-$C_3$ alkoxy;
and the pharmaceutically acceptable salts thereof.

8. The method of claim 7 wherein in the compound administered, $R_1$ is $C_1$-$C_8$ alkyl, $R_2$ is hydrogen, and $R_4$ is hydroxy.

9. The method according to claim 8 wherein the compound administered in cis 1,3-dimethyl-4-n-propyl-4-(3-hydroxyphenyl)piperidine.

10. The method of claim 8 wherein the compound is administered as a pharmaceutically acceptable salt.

* * * * *